(12) United States Patent
Chou et al.

(10) Patent No.: US 6,327,037 B1
(45) Date of Patent: Dec. 4, 2001

(54) OPTICAL ROTATION ANGLE POLARIMETER

(75) Inventors: Chien Chou, 5F, No. 37-3, Chuan-Yuan Rd., Pei-Tou Dist., Taipei City; Chien-Yuan Han, Kaohsiung; Wen-Chuan Kuo, Taipei, all of (TW)

(73) Assignee: Chien Chou, Taipei (TW)

( * ) Notice: Subject to any disclaimer, the term of this patent is extended or adjusted under 35 U.S.C. 154(b) by 0 days.

(21) Appl. No.: 09/294,530

(22) Filed: Apr. 19, 1999

Related U.S. Application Data

(63) Continuation-in-part of application No. 08/967,691, filed on Nov. 12, 1997, now Pat. No. 5,896,198.

(51) Int. Cl.$^7$ .................................................. G01B 9/02
(52) U.S. Cl. ...................................... 356/484; 356/487
(58) Field of Search .................................. 356/349, 351, 356/345

(56) References Cited

U.S. PATENT DOCUMENTS

| | | | |
|---|---|---|---|
| 4,671,657 | * | 6/1987 | Calvani et al. ...................... 356/349 |
| 4,750,830 | | 6/1988 | Lee . |
| 4,777,953 | | 10/1988 | Ash et al. . |
| 4,854,322 | | 8/1989 | Ash et al. . |
| 5,209,231 | | 5/1993 | Cote et al. . |
| 5,331,400 | * | 7/1994 | Wilkening et al. .................. 356/349 |
| 5,341,805 | | 8/1994 | Stavridi et al. . |
| 5,379,764 | | 1/1995 | Barnes et al. . |
| 5,398,681 | | 3/1995 | Kupershmidt . |
| 5,433,197 | | 7/1995 | Stark . |
| 5,448,992 | | 9/1995 | Kupershmidt . |
| 5,477,327 | | 12/1995 | Bergman . |
| 5,533,509 | | 7/1996 | Koashi et al. . |
| 5,535,743 | | 7/1996 | Backhaus et al. . |
| 5,560,356 | | 10/1996 | Peyman . |
| 5,586,133 | | 12/1996 | Sommargren . |
| 5,671,301 | | 9/1997 | Kupershmidt . |
| 5,672,875 | | 9/1997 | Block et al. . |
| 5,896,198 | * | 4/1999 | Chou et al. ............................ 356/349 |
| 5,910,840 | * | 6/1999 | Fürstenau ............................. 356/351 |

OTHER PUBLICATIONS

Rabinovitch et al., "Noninvasive Glucose Monitoring of the Aqueous Humor of the Eye: Part I. Measurement of Very Small Optical Rotations," *Diabetes Care*, 5(3):254–258 (1982).

March et al., "Noninvasive Glucose Monitoring of the Aqueous Humor of the Eye: Part II. Animal Studies and the Scleral Lens," *Diabetes Care*, 5(3):259–265 (1982).

Otani et al., "Light Source With Orthogonally Linear Polarized Two–Frequency Beam From Laser Diode and Surface Profile Measurement," *Society of Photo Optical Instrumentation Engineers*, (35)4:10701073 (1996).

\* cited by examiner

Primary Examiner—Frank G. Font
Assistant Examiner—Phil Natividad

(57) ABSTRACT

In an optical rotation angle polarimeter for investigating optical activity of a test object, a two-frequency laser source generates a laser beam with two eigen modes of two different temporal frequencies and two orthogonal linear polarized waves. The laser beam is to be passed through the test object. The polarized beam splitter is adapted to receive and split the laser beam, which exits the test object, into first and second orthogonal optical heterodyne interference X-axis and Y-axis components. Each of first and second photo detectors receives a respective one of the first and second orthogonal optical heterodyne interference X-axis and Y-axis components from the polarized beam splitter, and generates a corresponding optical heterodyne interference signal. A signal processor is connected to the first and second photo detectors, and combines the optical heterodyne interference signals therefrom so as to obtain an optical heterodyne interference output. An amplitude detector detects the amplitude of the optical heterodyne interference output, which serves as a measure of the optical activity of the test object. In addition, the laser beam has an adjustable wavelength to permit measurement of dispersion of optical rotation angles versus wavelength for an optically active material or substance.

19 Claims, 4 Drawing Sheets

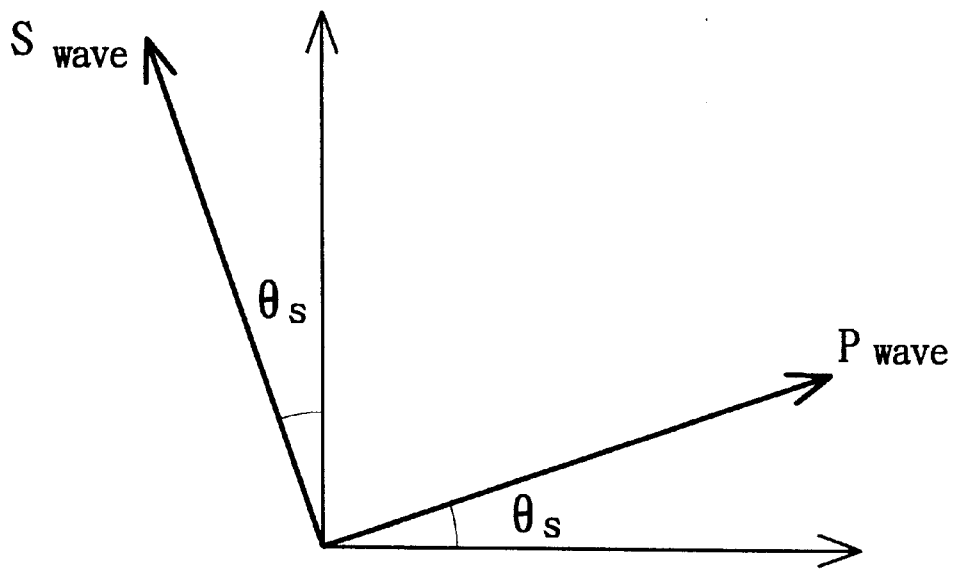
F I G. 3a
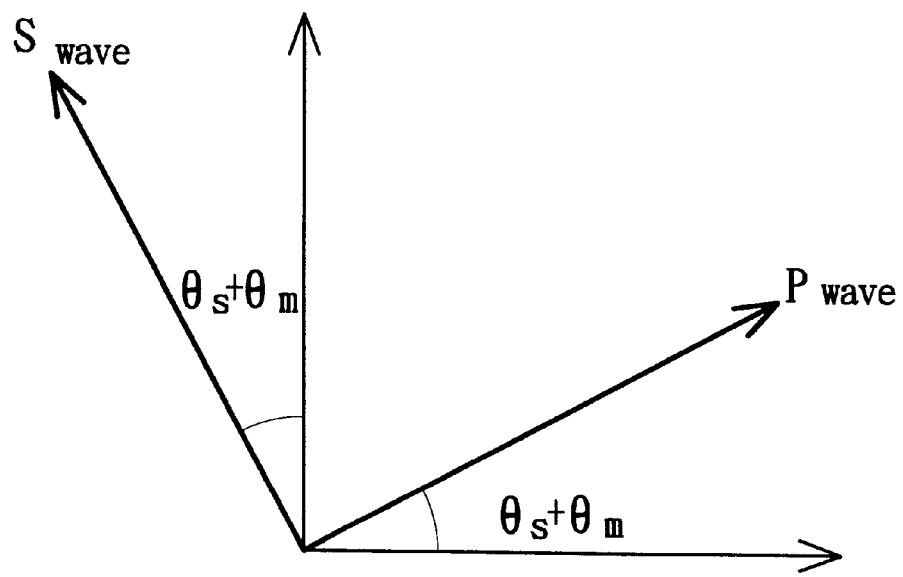
F I G. 3b

OPTICAL ROTATION ANGLE POLARIMETER

CROSS-REFERENCE TO RELATED APPLICATION

This is a continuation-in-part of U.S. patent application Ser. No. 08/967,691, now U.S. Pat. No. 5,896,198, entitled "Optical Heterodyne-Based Method and Apparatus for Determining the Concentration of Optically Active Substances," filed on Nov. 12, 1997, and having a common inventor with this application.

BACKGROUND OF THE INVENTION

1. Field of the Invention

The invention relates to an optical rotation angle polarimeter, more particularly to a noninvasive optical rotation angle polarimeter, which can be used to investigate the optical activity of optically active materials or substances.

2. Description of the Related Art

Polarizers and analyzers, in combination with mechanical methods for generating intensity-modulated signals, have been used to measure directly the optical rotation angle introduced by an optically active material or substance on linear polarized light to determine a physical property of the optically active material or substance, such as the refractive index of solid optically active materials or the concentration of optically active substances in a solution. Because of the susceptibility of the intensity-modulated signals generated by conventional mechanical methods to vibrations, and the relatively low frequency of the intensity-modulated signals that make it difficult to achieve high measuring precision, and because of the relatively slow measuring speed that results when conventional mechanical methods are in use, the conventional mechanical methods are currently being replaced with optic modulators, such as acousto-optic, electro-optic or photoelastic modulators, as intensity-modulated incident light sources. With the use of optic modulators, the magnitude of the optical rotation angle can be obtained by measuring directly the amplitude or phase of an intensity-modulated output light signal. However, because optic modulators are unstable, the high frequency intensity-modulated signals or polarization modulation signals generated thereby are prone to errors. Although a relatively high modulating frequency and relatively high stability can be achieved when optical heterodyne interference is generated in conjunction with acousto-optic modulators, the interferometer is very sensitive to disturbance from the outside environment, which can lead to limitations in the measuring precision of the system.

In co-pending U.S. patent application Ser. No. 08/967,691, there is disclosed a method and apparatus for determining the concentration of an optically active substance in a medium. In the disclosed method, a laser beam with two eigen modes of two different frequencies and two orthogonal linear polarized states is generated and passed through the medium. Then, the laser beam that exits the medium is passed through an analyzing polarizer so as to generate an optical heterodyne of the orthogonal linear polarized states. The amplitude of the optical heterodyne is detected for subsequent conversion into the concentration of the optically active substance in the medium. The method and apparatus are suitable for noninvasive in vivo glucose monitoring of the aqueous humor in an eye of an animal.

SUMMARY OF THE INVENTION

The object of the present invention is to provide an optical rotation angle polarimeter that can be used to measure the optical rotation angle introduced by optically active materials or substances, that is not easily disturbed by the outside environment, that has a relatively simple construction, that can achieve relatively high measuring precision, and that can permit real-time optical rotation angle measurement to monitor a physical property of the optically active materials or substances, such as the refractive index of solid optically active materials or the concentration of optically active substances in a medium.

More particularly, the object of the present invention is to provide an optical rotation angle polarimeter that utilizes a two-frequency laser with two orthogonal linear polarized states as a light source, in conjunction with a polarized beam splitter to generate an optical heterodyne interference signal, whose amplitude is subsequently measured to obtain the optical rotation angle.

According to the present invention, an optical rotation angle polarimeter is used to investigate optical activity of a test object, and comprises:

a two-frequency laser source for generating a laser beam with two eigen modes of two different temporal frequencies and two orthogonal linear polarized waves, the laser beam to be passed through the test object;

a polarized beam splitter adapted to receive and split the laser beam, which exits the test object, into first and second orthogonal optical heterodyne interference X-axis and Y-axis components;

first and second photo detectors, each of which receives a respective one of the first and second orthogonal optical heterodyne interference X-axis and Y-axis components from the polarized beam splitter and generates a corresponding optical heterodyne interference signal;

a signal processor, connected to the first and second photo detectors, for combining the optical heterodyne interference signals therefrom so as to obtain an optical heterodyne interference output; and an amplitude detector for detecting amplitude of the optical heterodyne interference output, which serves as a measure of the optical activity of the test object.

Preferably, a computer is connected to the amplitude detector, and converts the amplitude of the optical heterodyne interference output detected by the amplitude detector into an optical rotation angle introduced by the test object into the laser beam that passes therethrough.

BRIEF DESCRIPTION OF THE DRAWINGS

Other features and advantages of the present invention will become apparent in the following detailed description of the preferred embodiments with reference to the accompanying drawings, of which:

FIG. 3a illustrates shifting of the orthogonal linear polarized waves of FIG. 2a by an azimuth angle θs after calibration of the first embodiment and when no optical activity is detected;

FIG. 3b illustrates the optical rotation angle θm that affects the orthogonal linear polarized waves of FIG. 3a after the latter pass through a test object.

DETAILED DESCRIPTION OF THE PREFERRED EMBODIMENTS

Figure 1:
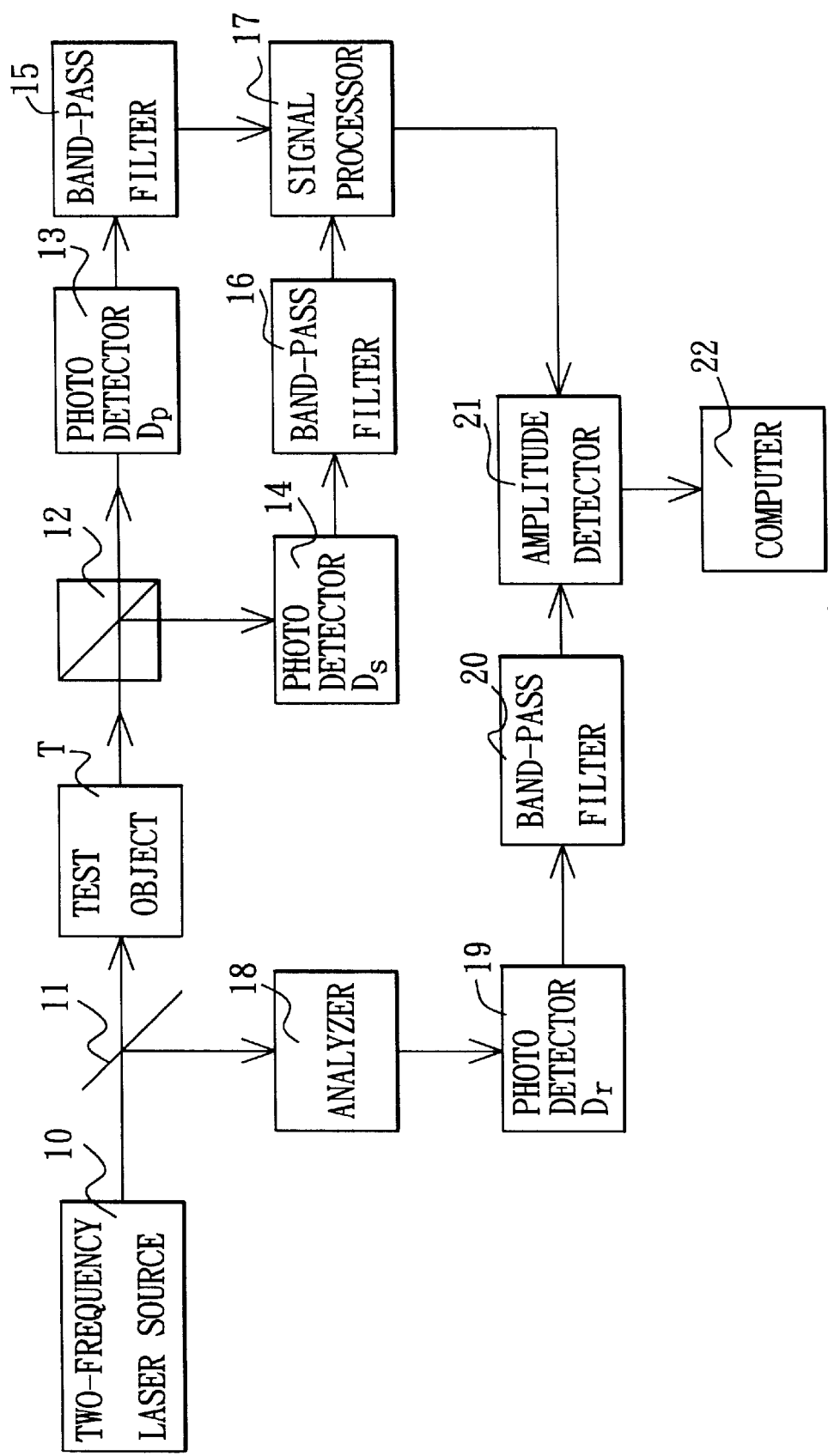
FIG. 1 is a block diagram illustrating the first preferred embodiment of an optical rotation angle polarimeter according to the present invention.

Before the present invention is described in greater detail, it should be noted that like elements are denoted by the same reference numerals throughout the disclosure.

Figure 2A:
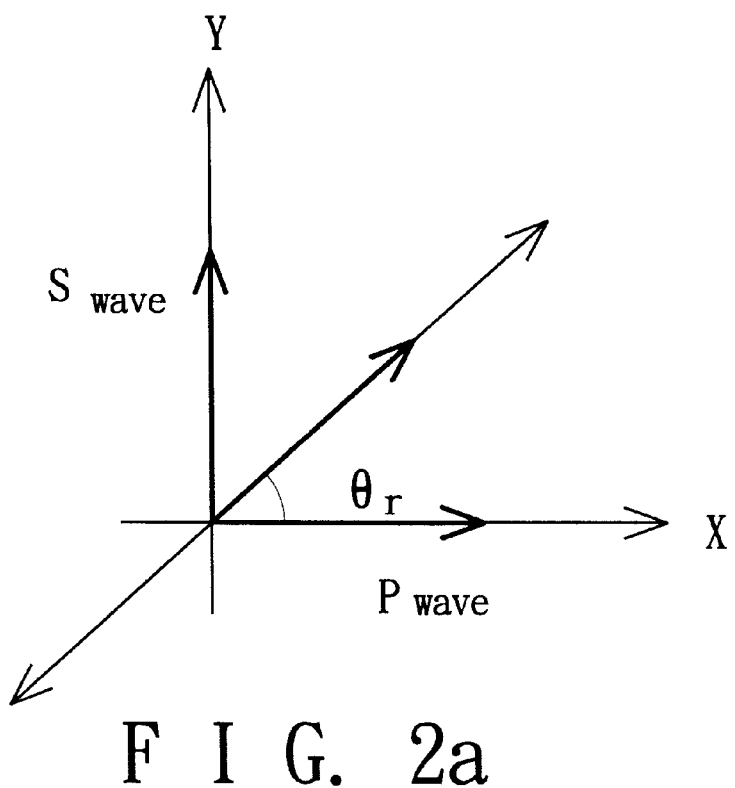
FIG. 2a illustrates the relationship among two orthogonal linear polarized waves of a two-frequency laser source and an azimuth angle θr of an optical analyzer of the first preferred embodiment.

Referring to FIG. 1, the first preferred embodiment of an optical rotation angle polarimeter according to the present invention is shown to comprise a linear polarized two-frequency laser source 10, a beam splitter 11, a polarized beam splitter (PBS) 12, a first photo detector (Dp) 13, a second photo detector (Ds) 14, a first band-pass filter 15, a second band-pass filter 16, a signal processor 17, an optical analyzer 18, a third photo detector (Dr) 19, a third band-pass filter 20, an amplitude detector 21, and a computer 22. The laser source 10 generates a linear polarized output laser beam having two eigen modes of two different temporal frequencies, $\omega_1$, $\omega_2$, and two orthogonal linear polarized waves that include a P wave parallel to the X-axis and an S wave parallel to the Y-axis, as shown in FIG. 2a. The output laser beam propagates along the Z-axis. The laser source 10 may be a gas or solid state two-frequency laser, such as a Zeeman laser or a laser diode. Alternatively, the laser source 10 may be formed from a stabilized linear polarized single-frequency laser, a polarized beam splitter, and two sets of phase modulators having different driving frequencies, such as the one disclosed in the aforesaid co-pending U.S. Patent application. In another example of the laser source 10, a single-frequency linear polarized semiconductor laser is used in combination with optical polarizers and current modulators to generate the desired output laser beam. Preferably, the wavelength of the output laser beam is adjustable so as to be adapted for use in the measurement of the dispersion of the optical rotation angles versus wavelength.

The beam splitter 11 is disposed at the output side of the laser source 10, and splits the output laser beam into a reference beam and a test beam.

Figure 2B:
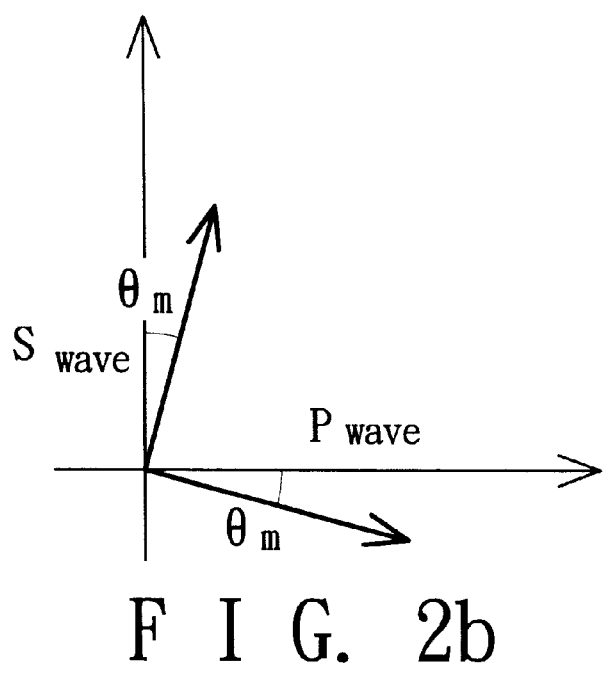
FIG. 2b illustrates the optical rotation angle θm that affects the orthogonal linear polarized waves of FIG. 2a after the latter pass through a test object with optical activity.

The test beam passes through a test object (T) before reaching the polarized beam splitter (PBS) 12. The test object (T) can be a solid optically active material, or a solution that contains an optically active substance. The test object (T) introduces an optical rotation angle $\theta m$ to the test beam passing therethrough, as shown in FIG. 2b. The polarized beam splitter (PBS) 12 splits the test beam exiting the test object (T) into the orthogonal optical heterodyne interference X-axis and Y-axis components. The polarized beam splitter (PBS) 12 can be a cubic polarized beam splitter, an optic fiber polarized beam splitter, or a thin-film polarized beam splitter. For a cubic polarized beam splitter, the edges thereof are preferably coincident with the X axis and the Y-axis of the coordinate, the Z-axis being the propagation direction of the laser beam. The first and second photo detectors 13, 14 receive the X-axis and Y-axis components of the test beam from the polarized beam splitter (PBS) 12. The first and second photo detectors 13, 14, which have a fast frequency response, can be a photo diode or a photo multiplier. The outputs of the first and second photo detectors 13, 14 are optical heterodyne interference signals that can be expressed as follows:

$$I_x(\Delta\omega t) = a_1 a_2 \sin(2\theta m)\cos(\Delta\omega t) + DC \qquad (1)$$

$$I_y(\Delta\omega t) = a_1 a_2 \sin(\pi + 2\theta m)\cos(\Delta\omega t) + DC \qquad (2)$$

in which $a_1$, $a_2$ are the amplitudes of the orthogonal wave components, $\Delta\omega = \omega_1 - \omega_2$, and DC is a direct current component.

When the optical rotation angle $\theta m$ introduced by the test object (T) to the test beam is very small, Equations (1) and (2) can be rewritten as follows:

$$I_x(\Delta\omega t) = 2a_1 a_2 \theta m \cos(\Delta\omega t) + DC \qquad (3)$$

$$I_y(\Delta\omega t) = -2a_1 a_2 \theta m \cos(\Delta\omega t) + DC \qquad (4)$$

The outputs of the first and second photo detectors 13, 14 are received respectively by the first and second band-pass filters 15, 16. Each of the band-pass filters 15, 16 processes the corresponding input thereto to obtain an intensity-modulated signal output, and has a center frequency set at the beat frequency ($\Delta\omega$) of the output laser beam from the laser source 10. The signal processor 17 is connected to the band-pass filters 15, 16, and generates an optical heterodyne interference output by combining the modulated signal outputs of the band-pass filters 15, 16. In this embodiment, the signal processor 17 generates the difference between the modulated signal outputs of the band-pass filters 15, 16 according to the following equation:

$$I_o = I_x - I_y = 4a_1 a_2 \theta m \cos(\Delta\omega t) \qquad (5)$$

The amplitude detector 21, such as a digital voltmeter or a lock-in amplifier, is connected to the signal processor 17, and detects the amplitude of the optical heterodyne interference output with a fixed beat frequency ($\Delta\omega$). The computer 22, such as a personal computer, is connected to the amplitude detector 21, and converts the detected amplitude from the latter into the optical rotation angle $\theta m$. A physical property of the test object (T), such as the concentration of an optically active substance in case the test object (T) is a solution, or the refractive index in case the test object (T) is a solid optically active material, can be determined by the computer 22 from the detected amplitude at this time. According to Equation 5, the amplitude of the signal corresponding to the test beam that exits the test object (T) is equal to $4a_1 a_2 \theta m$. As such, there is a linear relationship between the strength of the signal and the optical rotation angle introduced by the test object (T). In the present invention, the polarized beam splitter (PBS) 12 can increase the sensitivity of the polarimeter by up to two-fold as compared to when an analyzing polarizer (not shown) is in use.

The analyzer 18 is a linear analyzing polarizer having a fixed azimuth angle $\theta r$ (see FIG. 2a), and has the reference beam from the beam splitter 11 passing therethrough. The third photo detector 19, which has a fast frequency response, detects the reference beam through the analyzer 18, and generates a reference optical heterodyne signal corresponding to the reference beam that was detected thereby and having a beat frequency ($\Delta\omega$). Like the first and second photo detectors 13, 14, the third photo detector 19 can be a photo diode or a photo multiplier. The third band-pass filter 20, which has a center frequency set at the beat frequency ($\Delta\omega$) of the output laser beam from the laser source 10, is connected to the third photo detector 19, and processes the signal therefrom. The amplitude detector 21 is connected to the third band-pass filter 20 to receive the output of the latter. By detecting the amplitude of the reference output from the third band-pass filter 20, the strength of the output laser beam from the laser source 10 can be monitored and calibrated. The reference output from the third band-pass filter 20 can also serve as a reference signal for the amplitude detector 21 in case a lock-in amplifier is used for the latter.

In FIG. 3a, the polarimeter is calibrated such that the P wave and S wave of the output laser beam form an azimuth angle θs with respect to the corresponding one of the X and Y axes. Under this condition, when the optical rotation angle θm is introduced into the laser beam after the latter passes through the test object (T), as shown in FIG. 3b, the optical heterodyne interference signals from the first and second photo detectors 13, 14 can be expressed as follows:

$$I_x(\Delta\omega t)=a_1 a_2 \sin 2(\theta s+\theta m)\cos(\Delta\omega t)+DC \quad (6)$$

$$I_y(\Delta\omega t)=-a_1 a_2 \sin 2(\theta s+\theta m)\cos(\Delta\omega t)+DC \quad (7)$$

When the sum of the azimuth angle θs and the optical rotation angle θm introduced by the test object (T) to the laser beam is very small, Equations (6) and (7) can be rewritten as follows:

$$I_x(\Delta\omega t)=2a_1 a_2(\theta s+\theta m)\cos(\Delta\omega t)+DC \quad (8)$$

$$I_y(\Delta\omega t)=-2a_1 a_2(\theta s+\theta m)\cos(\Delta\omega t)+DC \quad (9)$$

As such, under the condition that no optical activity is present, the photo detectors 13, 14 will generate a signal with a constant oscillating frequency, thereby eliminating the adverse effects of low frequency noise interference on the operation of the signal processor 17, and increasing the sensitivity of the polarimeter.

The combining operation of the signal processor 17 should not be limited to the one described beforehand. In practice, the signal processor 17 can also be designed to generate an output according to the following equation:

$$|I_o'|=\sqrt{I_x^2(\Delta\omega t)+I_y^2(\Delta\omega t)}=2\sqrt{2}a_1 a_2 \theta m \quad (10)$$

Therefore, by varying the design of the signal processor 17, the sensitivity of the polarimeter can also be varied correspondingly.

Figure 4:
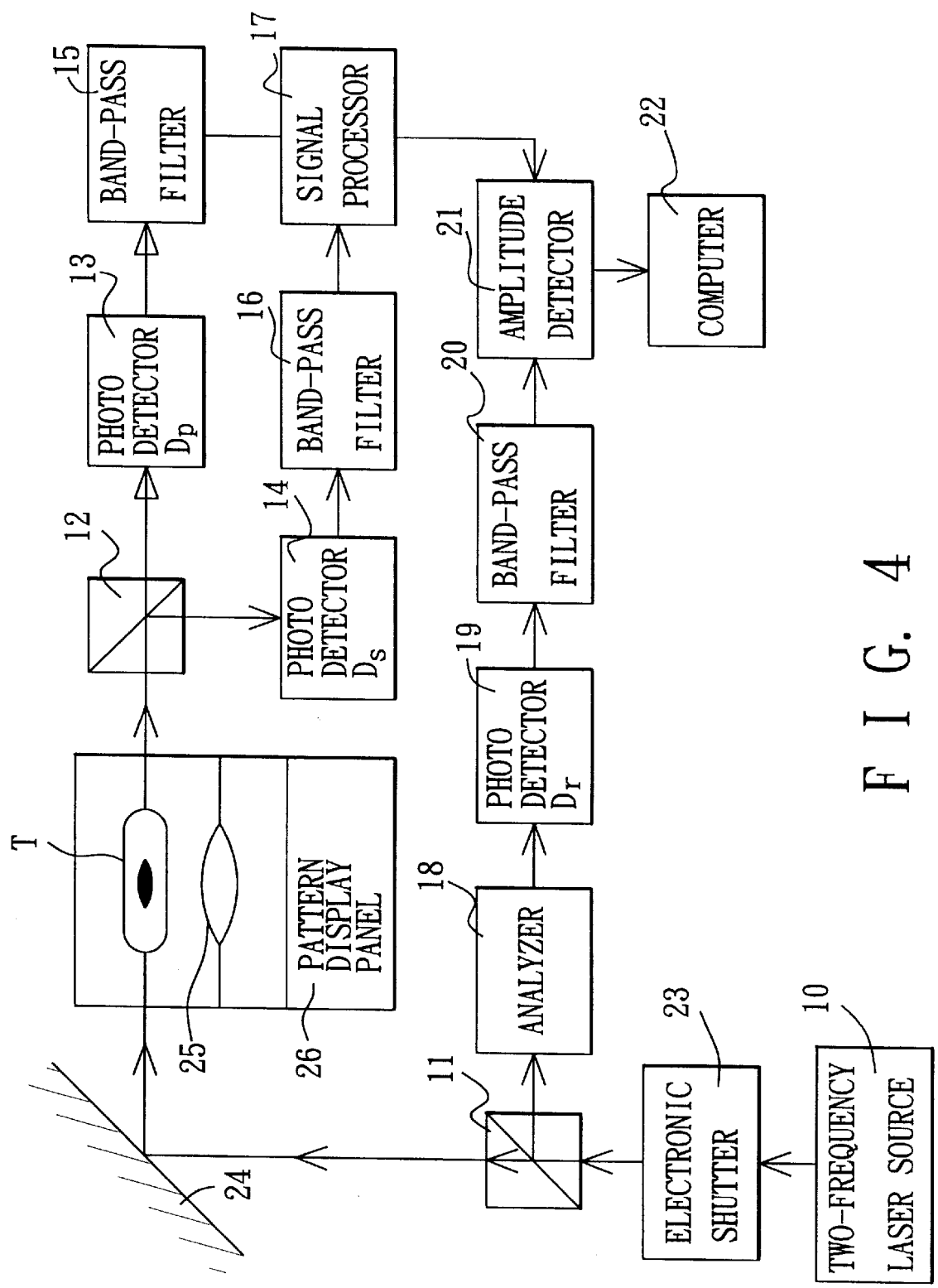
FIG. 4 is a block diagram illustrating the second preferred embodiment of an optical rotation angle polarimeter according to the present invention.

FIG. 4 illustrates the second preferred embodiment of an optical rotation angle polarimeter according to the present invention. Unlike the embodiment of FIG. 1, the second preferred embodiment is suitable for noninvasive in vivo glucose monitoring. The test object (T) is an animal or human eye, and the optically active substance is glucose in the aqueous humor of the animal or human eye. Blood glucose concentration can be determined once the optical rotation angle attributed to the glucose in the aqueous humor has been measured.

As shown in FIG. 4, when compared with the embodiment of FIG. 1, the second preferred embodiment further includes an electronic shutter 23, a mirror 24, a lens set 25 and a pattern display panel 26.

The electronic shutter 23 is interposed between the laser source 10 and the beam splitter 11. After being reflected by a 90° angle by the mirror 24, the test beam from the beam splitter 11 is passed laterally through the cornea and the aqueous humor in the eye (T) of a patient, before reaching the polarized beam splitter (PBS) 12. The polarized beam splitter (PBS) 12, the first and second photo detectors 13, 14, the first and second band-pass filters 15, 16, the signal processor 17, and the amplitude detector 21 then operate in a manner similar to that described beforehand in connection with the embodiment of FIG. 1. The optical rotation angle determined by the computer 22, however, is further converted by the computer to measure the blood glucose concentration of the patient.

As to the analyzer 18, the third photo detector 19, and the third band-pass filter 20, they also function in a manner similar to that described in connection with the embodiment of FIG. 1.

In the embodiment of FIG. 4, the lens set 25 and the pattern display panel 26 cooperate to present a visual image for fixing the eye (T) of the patient during noninvasive in vivo glucose monitoring.

In addition, in the present invention, different output wavelengths of the laser source 10 can be used to measure the dispersion of the optical rotation angles versus wavelength for the optically active material or substance.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

We claim:

1. An optical rotation angle polarimeter for investigating optical activity of a test object, comprising:

a two-frequency laser source for generating a laser beam with two eigen modes of two different temporal frequencies and two orthogonal linear polarized waves, the laser beam to be passed through the test object;

a polarized beam splitter adapted to receive and split the laser beam, which exits the test object, into first and second orthogonal optical heterodyne interference X-axis and Y-axis components;

first and second photo detectors, each of which receives a respective one of the first and second orthogonal optical heterodyne interference X-axis and Y-axis components from said polarized beam splitter and generates a corresponding optical heterodyne interference signal;

a signal processor, connected to said first and second photo detectors, for combining the optical heterodyne interference signals therefrom so as to obtain an optical heterodyne interference output; and an amplitude detector for detecting amplitude of the optical heterodyne interference output, which serves as a measure of the optical activity of the test object.

2. The optical rotation angle polarimeter as claimed in claim 1, further comprising first and second band-pass filters for interconnecting said signal processor and a respective one of said first and second photo detectors.

3. The optical rotation angle polarimeter as claimed in claim 2, wherein each of said first and second band-pass filters has a center frequency set at a beat frequency of the two different temporal frequencies.

4. The optical rotation angle polarimeter as claimed in claim 1, wherein said signal processor combines the optical heterodyne interference signals from said first and second photo detectors by obtaining a difference thereof.

5. The optical rotation angle polarimeter as claimed in claim 1, wherein said signal processor combines the optical heterodyne interference signals from said first and second photo detectors by obtaining square root of a sum of squares of the optical heterodyne interference signals.

6. The optical rotation angle polarimeter as claimed in claim 1, further comprising a computer connected to said amplitude detector for converting the amplitude of the optical heterodyne interference output detected by said amplitude detector into an optical rotation angle introduced by the test object into the laser beam that passes therethrough.

7. The optical rotation angle polarimeter as claimed in claim 6, wherein the test object is a solid optically active material, and said computer further converts the optical rotation angle into a refractive index of the test object.

8. The optical rotation angle polarimeter as claimed in claim 6, wherein the test object is a solution that contains an optically active substance, and said computer further converts the optical rotation angle into concentration of the optically active substance in the solution.

9. The optical rotation angle polarimeter as claimed in claim 1, further comprising:
- a beam splitter adapted to be disposed between said laser source and the test object to split the laser beam into a test beam that is to be passed through the test object, and a reference beam;
- an optical analyzer having the reference beam passing therethrough; and
- a third photo detector for receiving the reference beam from said optical analyzer and for generating a reference optical heterodyne interference signal corresponding thereto.

10. The optical rotation angle polarimeter as claimed in claim 9, further comprising a third band-pass filter interconnecting said third photo detector and said amplitude detector.

11. The optical rotation angle polarimeter as claimed in claim 10, wherein said third band-pass filter has a center frequency set at a beat frequency of the two different temporal frequencies.

12. The optical rotation angle polarimeter as claimed in claim 10, wherein the reference optical heterodyne interference signal from said third photo detector and processed by said third band-pass filter is received by said amplitude detector.

13. The optical rotation angle polarimeter as claimed in claim 12, wherein said amplitude detector is a digital voltmeter.

14. The optical rotation angle polarimeter as claimed in claim 12, wherein said amplitude detector is a lock-in amplifier.

15. The optical rotation angle polarimeter as claimed in claim 9, wherein said optical analyzer is a linear analyzing polarizer.

16. The optical rotation angle polarimeter as claimed in claim 6, wherein the test object is a human eye, and said computer further converts the optical rotation angle into concentration of glucose in aqueous humor of the human eye.

17. The optical rotation angle polarimeter as claimed in claim 16, further comprising an electronic shutter adapted to be disposed between said laser source and the test object.

18. The optical rotation angle polarimeter as claimed in claim 16, further comprising a lens set and a pattern display panel which cooperatively present a visual image for fixing the human eye under test.

19. The optical rotation angle polarimeter as claimed in claim 1, wherein the laser beam has an adjustable wavelength to permit measurement of dispersion of optical rotation angles versus wavelength for an optically active material or substance.

\* \* \* \* \*